United States Patent [19]
Olliero et al.

[11] Patent Number: 5,250,725
[45] Date of Patent: Oct. 5, 1993

[54] AROMATIC ACID INTERMEDIATES

[75] Inventors: Dominique Olliero; Bernard Labeeuw, both of Montpellier; Gilles Roche, Saint Jean De Vedas; Ali Salhi, Saint Gely du Fesc, all of France

[73] Assignee: Elf Sanofi, Paris, France

[21] Appl. No.: 754,037

[22] Filed: Sep. 3, 1991

Related U.S. Application Data

[60] Division of Ser. No. 420,270, Oct. 13, 1989, Pat. No. 5,079,241, which is a continuation-in-part of Ser. No. 121,846, Nov. 17, 1987, abandoned, and Ser. No. 254,822, Oct. 7, 1988, abandoned.

[30] Foreign Application Priority Data

Nov. 20, 1986 [FR] France .................. 86 16175
Oct. 8, 1987 [FR] France .................. 87 13925

[51] Int. Cl.$^5$ ............................ C07C 311/17
[52] U.S. Cl. .................... 562/430; 562/429; 540/222
[58] Field of Search ............ 562/430, 432, 424

[56] References Cited

U.S. PATENT DOCUMENTS

| | | | |
|---|---|---|---|
| 4,344,862 | 8/1982 | Widder et al. | 562/430 |
| 4,950,661 | 8/1990 | Olliero et al. | 514/207 |
| 4,960,929 | 10/1990 | Bapenfuhs | 562/430 |

*Primary Examiner*—Nicholas S. Rizzo
*Attorney, Agent, or Firm*—Foley & Lardner

[57] ABSTRACT

The present invention relates to novel cephalosporin derivatives with improved pharmacokinetics, corresponding to the formula:

in which:

$R_1$, $R_2$ and $R_3$ represent a hydrogen atom, or $R_1$ and $R_2$ represent a hydrogen atom or a methyl group and $R_3$ represents a carboxyl group, or $$-\underset{R_2}{\overset{R_1}{C}}-$$

form a cyclobutyl group and $R_3$ represents a carboxyl group; and

A and B are different and occupy the meta and para positions of the benzene ring, one representing a hydroxyl group and the other being selected from the groups $$-NH-CO-\underset{R_4}{CH}-NH-R_5,$$

$$-NH-CO-CH_2-CH_2-NH_2,$$

$$-NH-CO-\langle\text{cyclohexyl-NH}\rangle,$$

and $-NH-SO_2-Alk-NH_2$ in which Alk denotes a $C_2-C_4$ lower alkylene group and also to the pharmaceutically acceptable salts and esters of the said derivatives.

It further relates to a process for the preparation of such cephalosporins and to pharmaceutical compositions in which they are present.

1 Claim, No Drawings

AROMATIC ACID INTERMEDIATES

CROSS REFERENCE TO RELATED APPLICATIONS

This application is a division of application Ser. No. 07/420,270, filed Oct. 13, 1980, now U.S. Pat. No. 5,079,241, which application is a continuation-in-part of co-pending applications Ser. No. 121,846, filed Nov. 17, 1987, now abandoned and Ser. No. 254,822, filed Oct. 7, 1988 now abandoned.

BACKGROUND OF THE INVENTION

The present invention relates to cephalosporin derivatives with improved pharmacokinetics, to a process for their preparation and to pharmaceutical compositions in which they are present. It further relates to a novel intermediate for synthesizing certain of the cephalosporin derivatives.

In French patent application no. 84 14 878 published on Mar. 28, 1986 under the number 2 570 702, the Applicant Company described a family of cephalosporin derivatives possessing a broad activity against both Gram-negative germs and Gram-positive germs.

These derivatives include, in particular, compounds substituted in the 3-position by a group:

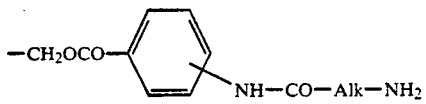

in which Alk represents an optionally substituted lower alkylene group and in which the substituent —NH—CO—Alk—NH$_2$ is located in the 3-position or 4-position.

According to the present invention, it has been found, surprisingly, that by slightly modifying the nature of the substituent in the 3-position, compounds are obtained which preserve the good activity of the compounds described in the prior art but additionally have greatly improved pharmacokinetic properties and, in particular, very high plasma concentrations which persist over a very long period.

Modification of the pharmacokinetic parameters in this way is important inasmuch as it opens up the possibility of reducing the dosage and the number of administrations of the product required for the same therapeutic effect.

DETAILED DESCRIPTION OF PREFERRED EMBODIMENTS

The compounds according to the invention correspond to the general formula:

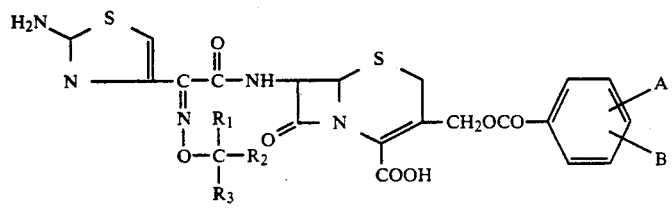

in which:

$R_1$, $R_2$ and $R_3$ each denote a hydrogen atom, or $R_1$ and $R_2$ each denote a hydrogen atom or a methyl group and $R_3$ denotes a carboxyl group, or $R_1$ and $R_2$, taken together with the carbon atom to which they are bonded, form a cyclobutyl ring and $R_3$ denotes a carboxyl group; and A and B are different and occupy the meta and para positions of the benzene ring, one representing an OH group and the other denoting either:

a group

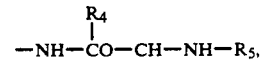

in which $R_4$ represents hydrogen, a methyl group, a hydroxymethyl group or a group —(CH$_2$)$_n$—NH$_2$, in which n is an integer between 1 and 4, and $R_5$ denotes hydrogen, or if $R_4$ represents hydrogen, $R_5$ can also represent a lower alkyl group containing from 1 to 4 carbon atoms; or a group —NH—CO—CH$_2$CH$_2$NH$_2$; or a group

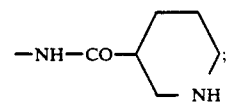

or a group —NH—SO$_2$—Alk—NH$_2$, in which Alk denotes a C$_2$-C$_4$ lower alkylene group.

Advantageously, the hydroxyl group (A or B) is in the meta position of the benzene ring.

As a consequence of the presence of an oxime group in their formula, the compounds (I) can exist in 2 isomeric forms: syn and anti. The syn isomers, which have the superior therapeutic activity, are the preferred compounds.

If one of the substituents A or B represents a group

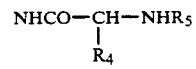

in which $R_4$ is other than hydrogen, the carbon atom carrying $R_4$ is an asymmetric carbon. The compounds (I) can therefore exist in the form of diastereoisomers (arising from the D or L forms of the amino acid) or in the form of a mixture of the 2 diastereoisomers (arising from the DL form of the amino acid). The invention encompasses all these forms.

Advantageously, the substituents A and B of the compounds according to the invention represent respectively, the hydroxyl group in the meta position, the —NHCOCH$_2$NH$_2$ group in the para position of the benzene ring.

(I)

It is understood that the compounds (I) indicated below can exist:
either in the form indicated in formula (I),
or in the tautomeric form (I'):

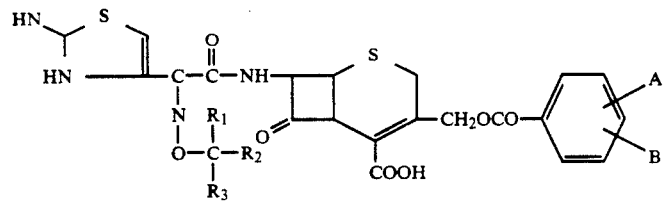
(I')

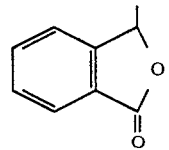

in which $R_1$, $R_2$, $R_3$, A and B are as defined above.

The salts of the compounds of formula I (or I') form an integral part of the invention.

These include salts with pharmaceutically acceptable acids which can be formed with the amino groups of the molecule, as well as salts with alkali metals or alkaline earth metals or salts with amino acids or amines, such as triethylamine or ethanolamines, which are capable of being formed with the carboxyl group in the 4-position of the compound (I) or, if it exists, with the carboxyl group present in the substituent of the oxime, or with both these carboxyl groups.

They can also be inner salts which can be formed between the carboxyl group (or groups) carried by the molecule and the primary amine groups present in the molecule on the substituent A or B, on the one hand, and the thiazole ring, on the other.

The same applies to the readily hydrolyzable or metabolically labile esters derived from one or other or both of the carboxyl groups which may be present in the molecule. Among these esters, the following may be mentioned in particular:

the phthalidyl esters:

the 1-acetoxyethyl esters:

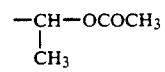

the 1-ethoxycarbonyloxyethyl esters:

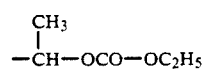

and
the (4-methyl-2-oxodioxol-4-en-5-yl)methyl esters:

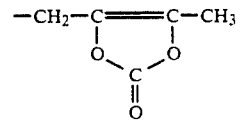

The invention also relates to processes for the preparation of the compounds of formula I (or I'), represented by the following reaction scheme:

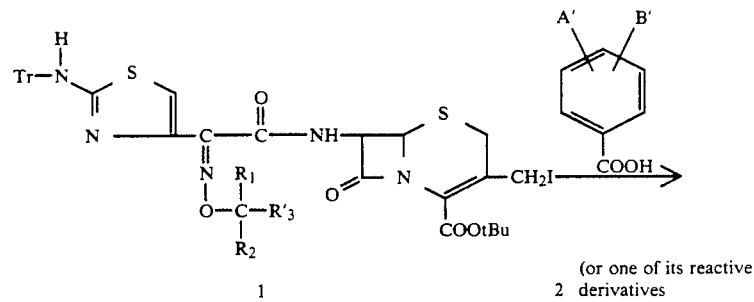

(or one of its reactive derivatives)

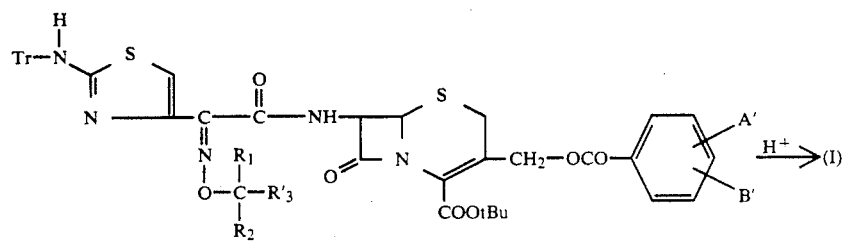

In these formulae, Tr represents a group protecting the amine group, preferably the trityl group, tBu represents the tert.-butyl group and $R'_3$ denotes hydrogen or a readily labile ester group, preferably a COOtBu group.

A' and B', which occupy the meta and para positions of the benzene ring, are different, one of them representing an OH group and the other representing a group derived from the other of the groups A and B by the blocking of the amino group or groups contained therein with a labile group.

Finally, $R_1$, $R_2$, and Alk have the meanings defined above.

The iodine compound 1 is reacted with the acid 2, (or one of its active derivatives) in which the amine group or groups have been protected beforehand, according to a known method, by a group such as tert.-butoxycarbonyl or trichloroethoxycarbonyl.

The reaction generally takes place in solution in a suitable solvent, preferably dimethylformamide, in the presence of potassium bicarbonate or a tertiary amine of low nucleophilicity, such as diisopropyl-ethylamine.

The reaction is carried out at a low temperature of 0° to 20° C.

The resulting protected compound 3 is used to prepare the compounds (I) by removal of the protecting groups carried by the amine and carboxyl groups, according to a known process, in particular by hydrolysis in an acid medium using, for example, trifluoroacetic acid or a mixture of formic acid with a strong acid such as hydrochloric acid or methanesulfonic acid.

Under these conditions, the compound (I) is isolated directly in the form of the salt of the amino group with the strong acid used for deprotection, i.e. in the form of the trifluoroacetate, hydrochloride, methane sulfonate, etc.

If desired, these salts can be converted to other salts of strong acids by passing a solution of the salt over a basic ion exchange resin in the form of the salt of a weak acid (for example formate or acetate).

The resulting solution is treated with the strong acid whose salt it is desired to obtain, and the resulting salt is isolated, for example by lyophilization.

The inner salts are prepared by desalification of the salts of strong acids obtained on deprotection, either by reaction with a base in an anhydrous medium or by passage through a column of ion exchange resin.

The iodine derivatives 1 used as starting materials are known or can be prepared by a known process, in particular as indicated in German Patent Application No. 3 311 300.

The protected amino acids 2 in which B' represents a blocked:

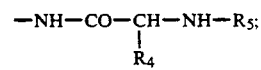

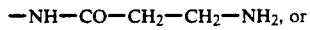

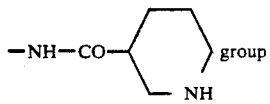

are prepared from the corresponding hydroxyamino acids according to the equation:

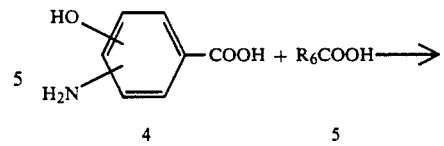

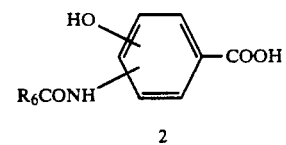

in which $R_6$ represents the groups corresponding to:

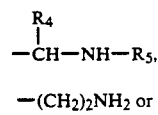

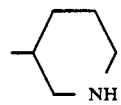

in which the amine group or groups have been protected and in which $R_4$ and $R_5$ are as defined above.

The reaction to form the amide is generally carried out not with the acid $R_6COOH$ but with an activated ester thereof, such as the ester of N-hydroxysuccinimide or the ester of N-hydroxybicyclo[2.2.1]hept-5-ene-2,3-dicarboxylic acid imide.

The reaction is carried out in solution in dimethylformamide by heating at between 30° and 80° C.

The protected amino acids 2 in which B' represents a blocked $-NH-SO_2-Alk-NH_2$ group are prepared from the corresponding hydroxyamino acids according to the equation:

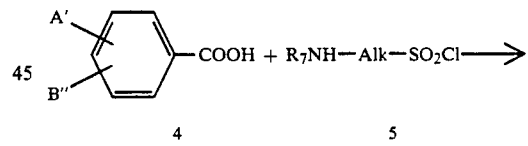

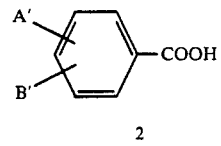

in which A' represents OH and B'' represents $NH_2$, and B' represents a group $R_7NH-Alk-SO_2NH-$, in which $R_7$ represents a protecting group for the amine group and in which Alk has the meaning indicated above.

The reaction is carried out in solution, for example in methylene chloride, in the presence of an acid acceptor and a reagent which activates the amine group and at the same time protects the carboxylic acid group. This is preferably done using trimethylchlorosilane.

The compounds 2 in which $R_7$ represents a given protecting group can be converted by acid hydrolysis into the product 2 in which $R_7$ is hydrogen, and then a compound 2 in which the amine group is protected by a different protecting group from the initial protecting group can be obtained by a known process.

The compounds of the formula

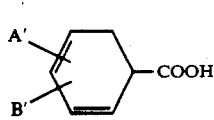

in which the groups A' and B' are different, one of them representing a group OH and the other representing a group X—NH—Alk—SO$_2$NH—, in which X represents hydrogen or a protecting group for the amine group and in which Alk is as defined above, are novel and in this respect form an integral part of the invention.

The carboxylic acid esters and salts of the compounds (I) of the invention are obtained from the compounds (I) by reactions known per se.

Thus, the inorganic salts are obtained by reacting the compounds (I) with an equimolecular amount of an inorganic base such as sodium hydroxide, potassium hydroxide or sodium bicarbonate; the salification reaction is carried out in a solvent such as water or ethanol, and the salt obtained is isolated by evaporation of the solution.

The salts of organic bases are obtained by reacting a solution of the acid I with an equimolecular amount of the organic base in a suitable solvent or mixture of solvents. The salt is isolated by precipitation with ether. The esters are obtained by the known esterification processes; for example, a halogen derivative will advantageously be reacted with a salt of the acid, such as the sodium salt; the reaction will preferably be carried out in a solvent which is capable of dissolving the starting acid derivative, for example in dimethylformamide.

The syn and anti isomeric forms are obtained by appropriately choosing the reactants.

The examples which follow will provide a clearer understanding of the scope of the invention without however limiting it.

As is usual in this family of compounds, the products according to the invention do not have sharp melting points, but only decomposition points which do not enable them to be characterized.

The products will therefore be characterized by their nuclear magnetic resonance spectra. Unless indicated otherwise, they are run at 250 MHz, with hexamethyldisiloxane as the internal standard.

The spectra are run in deuterated dimethyl sulfoxide: 10 mg in 0.5 mL.

The chemical shifts are measured to ±0.01 ppm and the coupling constants to ±0.5 Hz.

The following abbreviations will be used:
S: singlet
D: doublet
D of D: doublet of doublets
b.s.: broadened singlet
M: multiplet
Q: quadruplet
T: triplet
AB: AB system
J: coupling constant Elemental microanalyses were also performed in each case and are in agreement with the formulae indicated.

EXAMPLE 1

Bis-trifluoroacetate of 7-[2-(2-aminothiazol-4-yl)-2-(2-carboxyprop-2-yloxyimino)acetamido]-3-[[4-(2-aminoacetyl)amino-3-hydroxybenzoyl]oxymethyl]-3-cephem-4-carboxylic acid, syn isomer (SR 43753)

(I) R$_1$=R$_2$=—CH$_3$, R$_3$=—COOH, A=—OH (3), B=—NH—CO—CH$_2$—NH$_2$ (4)

A) 3-Hydroxy-4-[(2-tert.-butoxycarbonylaminoacetyl)amino]-benzoic acid

A solution of 9.75 g of 4-amino-3-hydroxybenzoic acid and 9.75 ml of triethylamine in 90 ml of dimethylformamide is heated to 80° C. 20 g of the N-hydroxysuccinimide ester of N-tert.-butoxycarbonylglycine are added and the reaction mixture is kept at 80° C. for 4 hours.

The solvent is evaporated off in vacuo and the residue is taken up in the minimum amount of water and poured into 2 liters of sulfate buffer pH 2.

The solid which separates out is filtered off, washed with water and dissolved in 1.2 liters of ethyl acetate. The organic solution is washed 3 times with 500 ml of water and then dried over magnesium sulfate. The solvent is evaporated off to dryness and the solid residue is taken up in 300 ml of methylene chloride, with vigorous stirring.

The crystals are filtered off, washed with methylene chloride and dried at 100° C. to give 16.5 g of the expected product. M.p.>250° C.

NMR SPECTRUM run at 60 MHz in solution in deuterated dimethyl sulfoxide: 1H at 9.13 ppm (S, ArNHCO) - 1H at 8.20 ppm (D, J=8 Hz, aromatic H meta COOH) - 2H at 7.47 ppm (M, aromatic protons ortho COOH) - 1H at 7.38 ppm (T, J= 7 Hz, —NH-Boc) - 2H at 3.77 ppm (D, J=7 Hz, —C(=O)—CH$_2$—N) - 9H at 1.30 ppm (S, —C(CH$_3$)$_3$)

B) Tert.-butyl 7-[2-(2-tritylaminothiazol-4-yl)-2-(2-tert.-butoxycarbonylprop-2-yloxyimino)acetamido]-3-[[4-(2-tert.-butoxycarbonylaminoacetyl)amino-3-hydroxybenzoyl]oxymethyl]-3-cephem-4-carboxylate, syn isomer 15 g of the protected acid prepared in A and 10.9 ml of diisopropylethylamine are dissolved in 100 ml of anhydrous dimethylformamide.

The solution is cooled to 4° C. and 36 g of tert.-butyl 7-[2-(2-tritylaminothiazol-4-yl)-2-(2-tert.-butoxycarbonylprop-2-yloxyimino)acetamido]-3-iodomethyl-3-cephem-4-carboxylate, syn isomer, are added. The reaction mixture is stirred at 4° C. for 5 hours and then poured into an iced solution of sulfate buffer pH 2. The resulting mixture is stirred vigorously for 10 minutes and the solid is then filtered off and washed with water. The solid is taken up in ethyl acetate and the organic solution is washed with sulfate buffer pH 2 followed by water, a saturated solution of sodium bicarbonate and finally water. The solution is dried over magnesium sulfate and the solvent is then evaporated off to dryness.

The product obtained is chromatographed on a column of silica H. Elution with a 90/10 (vol/vol) methylene chloride/ethyl acetate mixture gives 25 g of the expected product, which is used as such for the next step.

NMR SPECTRUM: 1H at 10.5 ppm (b.s., OH) - 1H at 9.35 ppm (D, J=9 Hz, —C(=O)—NH—) - 1H at 9.10 ppm (S, ArNHCO—) - 1H at 8.80 ppm (S, NH-trityl) - 1H at 8.15 ppm (D, J=8 Hz, aromatic H meta CO)

- 18H at 7.25 ppm (M, trityl aromatic protons, aromatic protons ortho CO and —NH-Boc)- 1H at 6.64 ppm (S, H thiazole) - 1H at 5.73 ppm (D of D, $J_1=9$ Hz, $J_2=4$ Hz, $H_7$) - 2H at 5.10 ppm (M, $H_6$ and $CH_2OC(=O)$—) - 1H at 4.81 ppm (D, J=13 Hz, CHHD 2OC=O) - 2H at 3.72 ppm (D, J=7 Hz, CO—$CH_2$—N)-2H at 3.57 ppm (AB, $J_{AB}=17$ Hz, $CH_2S$) - 33H at 1.30 ppm (3S, H-Boc and —C—$(CH_3)_2$)

C) SR 43753

25 g of the protected product obtained in B are added in small portions to a mixture of 250 ml of trifluoroacetic acid and 25 ml of anisole.

When the addition is complete, the mixture is left at 25° C. for 1 hour and then evaporated to dryness in vacuo. 500 ml of anhydrous ether are added to the residue and the resulting mixture is stirred vigorously for 15 minutes. The solid is filtered off, washed 3 times with anhydrous ether and then dried in vacuo.

18 g of the expected product are obtained:

NMR SPECTRUM: 1H at 10.60 ppm (b.s., OH) - 1H at 9.91 ppm (S, ArNHCO)-1H at 9.42 ppm (D, J=9 Hz, —CO—NH—) - 4H at 8.10 ppm (M, $NH_3^+$ glycine and aromatic H meta C=O) - 4H at 7.40 ppm (M, aromatic protons ortho CO and $NH_2$ thiazole)-1H at 6.71 ppm (S, H thiazole) - 1H at 5.82 ppm (D of D, $J_1=9$ Hz, $J_2=4$ Hz, $H_7$) - 2H at 5.20 ppm (M, $H_6$ and $CH_2OCO$) - 1H at 4.84 ppm (D, J=13 Hz, $CH_2OCO$)-2H at 3.85 ppm (M, CO—$CH_2$—N) - 2H at 3.64 ppm (AB, $J_{AB}=17$ Hz, $CH_2S$) - 6H at 1.40 ppm (2S, —N—O—C—$(CH_3)_2$)

EXAMPLES 2 TO 15

A) By following the same procedure as in Example 1-A, but varying the products reacted, the protected acids collated in Table 1 are obtained in the same manner.

TABLE 1

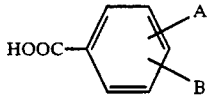

| A | B | NMR spectrum n° or melting point m.p.: |
|---|---|---|
| —NHCOCH$_2$NH—Boc | —OH | 1 |
| —OH | —NHCOCH$_2$CH$_2$NH—Boc | 2 |
| —OH | —NH—CO—CH(CH$_3$)—NH—Boc | 3 |
| —OH | —NHCO—CH(CH$_2$OH)—NHBoc | 4 |
| —OH | —NH—COCH$_2$—N(CH$_3$)—Boc | 5 |
| —OH | —NH—CO—<cyclohexyl-NBoc> | m.p.: 210-2° C. |
| —OH | —NH—CO—CH((CH$_2$)$_3$NH—Boc)—NH—Boc | 6 |
| —OH | —NH—CO—CH((CH$_2$)$_2$NHBoc)—NH—Boc | 7 |

NMR SPECTRUM No. 1 (60 MHz, DMSO): 1H at 12.60 ppm (b.s., COOH) - 1H at 10.40 ppm (b.s., OH) - 1H at 9.05 ppm (S, ArNH—) - 1H at 8.60 ppm (D, J=3 Hz, aromatic H ortho NH) - 1H at 7.57 ppm (D of D, $J_1=8$ Hz, $J_2=3$ Hz, aromatic H para NH) - 1H at 7.20 ppm (T, J=7 Hz, —NHBoc) - 1H at 6.90 ppm (D, J=8 Hz, aromatic H meta NH) - 2H at 3.72 ppm (D, J=7 Hz, —C(=O)—CH$_2$—N<) - 9H at 1.35 ppm (S, Boc)

NMR SPECTRUM No. 2: 1H at 12.50 ppm (b.s., COOH) - 1H at 10.43 ppm (b.s., OH) - 1H at 9.24 ppm (S, Ar—NH—) - 1H at 8.00 ppm (D, J=8 Hz, aromatic H ortho NH) - 1H at 7.40 ppm (S, aromatic H ortho OH) - 1H at 7.34 ppm (D, J=8 Hz, aromatic H para OH) - 1H at 6.81 ppm (T, J=7 Hz, NH-Boc) - 2H at 3.18 ppm (Q, J=7 Hz, —CH$_2$NH-Boc)-2H at 2.52 ppm (T, J=7 Hz, CH$_2$CH$_2$NHBoc) - 9H at 1.33 ppm (S, Boc)

NMR SPECTRUM No. 3 (60 MHz, DMSO): 1H at 12.40 ppm (b.s., COOH) - 1H at 10.40 ppm (b.s., OH) - 1H at 9.10 ppm (S, ArNH) - 1H at 8.10 ppm (D, J=8 Hz, aromatic H ortho NH) - 3H at 7.40 ppm (M, —NH-Boc+2 aromatic H) - 1H at 4.12 ppm

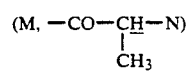

19H at 1.34 ppm (S, Boc) - 3H at 1.27 ppm

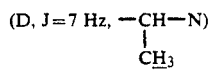
(D, J=7 Hz, —CH—N)
          |
          CH₃

NMR SPECTRUM No. 4: 1H at 12.60 ppm (b.s., COOH) - 1H at 10.45 ppm (b.s., Ar-OH) - 1H at 9.22 ppm (S, ArNHCO) - 1H at 8.18 ppm (D, J=8 Hz, aromatic H ortho NH) - 2H at 7.40 ppm (aromatic H meta NH) - 1H at 7.15 ppm (D, J=7 Hz, NHBoc) - 1H at 5.06 ppm (b.s., CH₂OH) - 1H at 4.17 ppm

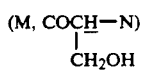
(M, COCH—N)
       |
       CH₂OH

- 2H at 3.57 ppm

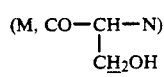
(M, CO—CH—N)
         |
         CH₂OH

- 9H at 1.34 ppm (S, Boc)

NMR SPECTRUM No. 5 (60 MHz, DMSO): 1H at 12.6 ppm (b.s., COOH) - 1H at 10.47 ppm (b.s., OH) - 1H at 9.21 ppm (S, ArNH—CO) - 1H at 8.10 ppm (D, J=8 Hz, aromatic H para OH) - 2H at 7.43 ppm (M, aromatic protons) - 2H at 4.00 ppm (S, COCH₂N) - 3H at 3.80 ppm (>N—CH₃) - 9H at 1.32 ppm (S, Boc)

NMR SPECTRUM No. 6: 1H at 12.66 ppm (b.s., COOH) - 1H at 10.44 ppm (b.s., OH) - 1H at 9.11 ppm (S, ArNHCO) - 1H at 8.12 ppm (D, J=8 Hz, aromatic H ortho NH) - 3H at 7.40 ppm

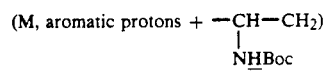
(M, aromatic protons + —CH—CH₂)
                          |
                          NHBoc

- 1H at 6.75 ppm (T, J=7 Hz, CH₂NHBoc) - 1H at 4.08 ppm

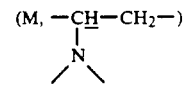
(M, —CH—CH₂—)
       |
       N
      / \

- 2H at 2.81 ppm (M, CH₂—N<) - 4H between 1.4 and 1.7 ppm (M, CH₂—CH₂) - 18H at 1.33 ppm (2S, Boc)

NMR SPECTRUM No. 7: 1H at 12.55 ppm (b.s., COOH) - 1H at 10.47 ppm (b.s., OH) - 1H at 9.15 ppm (S, ArNHCO) - 1H at 8.13 ppm (D, J=8 Hz, aromatic H ortho NH) - 3H at 7.40 ppm

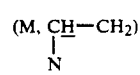
(M, aromatic protons + —CH—CH₂)
                          |
                          NHBoc

- 1H at 6.78 ppm (T, J=7 Hz, CH₂NHBoc) - 1H at 4.13 ppm

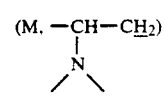
(M, CH—CH₂)
     |
     N

- 2H at 2.98 ppm (M, —CH₂NHBoc) - 1H at 1.92 ppm and 1H at 1.70 ppm

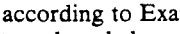
(M, —CH—CH₂)
       |
       N
      / \

- 18H at 1.33 ppm (2S, Boc)

B) Reaction of these protected acids with different iodine compounds according to Example 1-B gives the corresponding protected cephalosporins, which, when deprotected according to the method of Examples 1-C, lead to the different compounds (I) isolated in the syn form as the trifluoroacetates; these are collated in Table 2.

TABLE 2

| Example n° | SR code n° | R₁ | R₂ | R₃ | 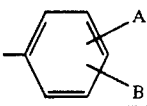 | NMR |
|---|---|---|---|---|---|---|
| 2 | 43851 | H | H | H | 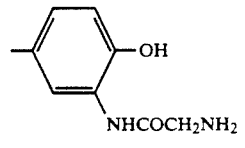 | 8 |
| 3 | 43852 | H | H | H | 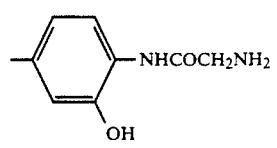 | 9 |
| 4 | 43853 | H | H | H | 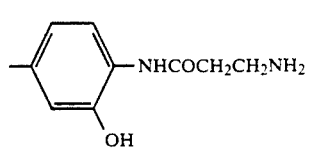 | 10 |

TABLE 2-continued

| Example n° | SR code n° | R₁ | R₂ | R₃ | Structure | NMR |
|---|---|---|---|---|---|---|
| 5 | 43903 | CH₃ | CH₃ | COOH | phenyl with -OH and -NHCOCH₂NH₂ | 11 |
| 6 | 43904 | CH₃ | CH₃ | COOH | phenyl with -NHCOCH₂CH₂NH₂ and -OH | 12 |
| 7 | 43955 | CH₃ | CH₃ | COOH | phenyl with -NH-COCH-NH₂, CH₃ (DL) and -OH | 13 |
| 8 | 43983 | H | H | H | phenyl with -NHCO-CH-NH₂, CH₂OH (L) and -OH | 14 |
| 9 | 43984 | CH₃ | CH₃ | COOH | " | 15 |
| 10 | 43985 | CH₃ | CH₃ | COOH | phenyl with -NHCOCH₂NHCH₃ and -OH | 16 |
| 11 | 44049 | CH₃ | CH₃ | COOH | phenyl with -NHCO-piperidinyl-NH and -OH (DL) | 17 |
| 12 | 44128 | CH₃ | CH₃ | COOH | phenyl with -NHCOCH(CH₂)₃NH₂, NH₂ (L) and -OH | 18 |
| 13 | 44130 | CH₃ | CH₃ | COOH | phenyl with -NHCOCH(CH₂)₂NH₂, NH₂ (DL) and -OH | 19 |
| 14 | 44218 | H | H | H | " | 20 |
| 15 | 44219 | H | H | H | phenyl with -NHCOCH(CH₂)₃NH₂, NH₂ (L) and -OH | 21 |

NMR SPECTRUM No. 8:1 H at 11.13 ppm (b.s., OH) - 1H at 9.80 ppm (s, ArNHCO) - 1H at 9.57 ppm (D, J=9 Hz, CONH) - 1H at 8.52 ppm (S, aromatic H ortho NH) - 3H at 8.02 ppm (b.s., CH₂—NH₃⁺) - 1H at 7.61 ppm (D, J=8 Hz, aromatic H para NH) - 2H at 7.25 ppm (b.s., NH$_2$ thiazole) - 1H at 6.98 ppm (D, J=8 Hz, aromatic H meta NH) - 1H at 6.70 ppm (S, H thiazole) - 1H at 5.77 ppm (D of D, J$_1$=9 Hz, J$_2$=4 Hz, H$_7$) - 1H at 5.20 ppm (D, J=13 Hz, CH$_2$OCO) - 1H at 5.16 ppm (D, J=4 Hz, H$_6$) - 1H at 4.85 ppm (D, J=13 Hz, CH$_2$OCO) - 3H at 3.77 ppm (S, NOCH$_3$) - 2H at 3.58 ppm (AB, J$_{AB}$=17 Hz, CH$_2$S)

NMR SPECTRUM No. 9: 1H at 10.57 ppm (b.s., OH) - 1H at 9.90 ppm (S, ArNHCO) - 1H at 9.61 ppm (D, J=9 Hz, CONH) - 4H at 8./10 ppm (M, aromatic H ortho NH and CH$_2$NH$_3^+$) - 4H at 7.40 ppm (aromatic protons meta NH and NH$_2$ thiazole) - 1H at 6.72 ppm (S, H thiazole) - 1H at 5.81 ppm (D of D, J$_1$=9 Hz, J$_2$=4 Hz, H$_7$) - 2H at 5.10 ppm (M, H$_6$ and CH$_2$OCO) - 1H at 4.90 ppm (D, J=13 Hz, CH$_2$OCO) - 2H at 3.85 ppm (M, CH$_2$NH$_2$) - 3H at 3.77 ppm (S, N—OCH$_3$) -2H at 3.65 ppm (AB, J$_{AB}$=17 Hz, CH$_2$S)

NMR SPECTRUM No. 10: 1H at 10.47 ppm (S, OH) - 2H at 9.54 ppm (M, CONH and ArNHCO) - 1H at 8.07 ppm (D, J=8 Hz, aromatic H ortho NH) - 3H at 7.80 ppm (b.s., CH$_2$NH$_3^+$) - 2H at 7.45 ppm (M, aromatic protons meta NH) - 2H at 7.20 ppm (b.s., NH$_2$ thiazole) - 1H at 6.70 ppm (S, H thiazole) - 1H at 5.78 ppm (D of D, J$_1$=0 Hz, J$_2$=4 Hz, H $_7$) - 2H at 5.13 ppm (M, H$_6$ and CH$_2$OCO) - 1H at 4.87 ppm (D, J=13 Hz, CHHD 2OCO) - 3H at 3.80 ppm (S, N—OCH$_3$) - 2H at 3.60 ppm (AB, J $_{AB}$=17 Hz, CH$_2$S) - 2H at 3.05 ppm (M, CH$_2$NH$_3^+$) - 2H at 2.80 ppm (M, CH$_2$CH$_2$NH$_3$)

NMR SPECTRUM No. 11: 1H at 11.20 ppm (b.s., OH) - 1H at 9.80 ppm (S, ArNHCO) - 1H at 9.56 ppm (D, J=9 H z, CONH) - 1H at 8.52 ppm (S, aromatic H ortho NH) - 3H at 8.06 ppm (b.s., CH$_2$NH$_3^+$) - 1H at 7.60 ppm (D, J=8 Hz, aromatic H para NH) -2H at 7.30 ppm (b.s., NH$_2$ thiazole) - 1H at 6.98 ppm (D, J=8 Hz, aromatic H meta NH) - 1H at 6.71 ppm (S, H thiazole) - 1H at 5.82 ppm (D of D, J$_1$=9 Hz, J$_2$=4 Hz, H$_7$) - 2H at 5.15 ppm (M, H$_6$ and CH$_2$OCO) - 1H at 4.81 ppm (D, J=13 Hz, CH$_2$OCO) - 2H at 3.84 ppm (M, CH$_2$NH$_3^+$) - 2H at 3.60 ppm (AB, J$_{AB}$=17 Hz, CH$_2$S) -

NMR Spectrum No. 12 1H at 10.48 ppm (b.s., OH)- 1H at 9.54 ppm (S, ArNHCO)-1H at p9.45 ppm (D, J=9 Hz, COHH)-1H at 8.10 ppm (D, J=8 Hz, aromatic H ortho NH)-2H at 7.70 ppm (b.s., CH$_N$H$_3^+$)-4H at 7.40 ppm (M, NH$_2$ thiazole, aromatic protons meta NH)-1H at 6.70 ppm (S, H thizzole)-1H at 5.80 ppm (D of D, J$_1$=9 Hz, J$_2$=4Hz, H$_7$)-2H at 5.15 ppm (M, H$_6$ and CH$_2$OCO)-1H at 4.82 ppm (D, J=13 Hz, CH$_2$OCO)-2H at 3.62 ppm (AB, J$_{AB}$=17 Hz, CH$_2$)-2H at 3.05 ppm (M, CH$_2$NH$_3^+$)-2H at 2.80 ppm (M, CH$_2$CH$_2$NH$_3^+$)-6 H at 1.34 ppm (2S, —C—(CH$_3$)$_2$) 6H at 1.35 ppm (2S, -C-()CH$_3$)$_2$)

NMR SPECTRUM No. 13: 1H at 10.60 ppm (b.s., OH) - 1H at 9.95 ppm (S, ArNHCO) - 1H at 9.47 ppm (D, J=9 Hz, CONH) - 4H at 8.20 ppm (M, —CH—HH$_3^+$ and aromatic protons ortho NH)
|
CH$_3$

- 4H at 7.40 ppm (M, NH$_2$ thiazole and aromatic protons metal NJ) - 1H at 6.71 ppm (S, H thiazole) - 1H at 5.88 ppm (D of D, J$_1$=9 Hz, J$_2$=4 Hz, H$_7$) - 2H at 5.20 ppm (M, H$_6$ and CH$_2$OCO) - 1H at 4.84 ppm (D, J=13 Hz, CH$_2$OCO) - 1H at 4.20 ppm (M, —CH—NH$_3^+$)
|
CH$_3$

- 2H at 3.62 ppm (AB, J$_{AB}$=17 Hz, CH$_2$S) - 9H at 1.35 ppm (M, —C—(CH$_3$)$_2$ and —CH—NH$_3^+$)
|
CH$_3$ NMR SPECTRUM No. 14: 1H at 10.62 ppm (b.b., OH) - 1H at 9.83 ppm (S, ArNHCO) - 1H at 9.59 ppm (D, J=9 Hz, CONH) - 4H at 8.30 ppm (M, CH—NH$_3^+$ and aromatic H ortho NH)
|
CH$_2$OH

- 2H at 7.43 ppm (M, aromatic protons meta NH) -2H t 7.25 ppm (b.s., NH$_2$ thiazole) - 1H at 6.69 ppm (S, Hthiazole) - 1H at 5.79 ppm (D of D, J$_1$=9 Hz, J$_2$=4 Hz, H$_7$) - 2H at 5.15 ppm (M, H$_6$ and CH$_2$OCO) - 1H at 4.86 ppm (D, J=13 H z, CHOCO) - 1H at 4.24 ppm (M, CH—NH$_3^+$)
|
CH$_2$OH

- 3H at 3.81 ppm (S, NOCH$_3$) - 2H at 3.76 ppm (D, J=6 Hz, CH—NH$_3^+$)
|
CH$_2$OH

- 2H at 3.63 ppm (AB, J$_{AB}$=17 Hz, CH$_2$S)

NMR SPECTRUM No. 15: 1H at 10.60 ppm (b, s., OH) - 1H at 9.90 ppm (S, ArNHCO) - 1H at 9.42 ppm (D, J=9 Hz, CONH) - 4H at 8.20 ppm (M, CH—NH$_3^+$ and aromatic H ortho NH)
|
CH$_2$OH

- 2H at 7.45 ppm (M, aromatic protons meta NH) - 2H at 7.30 ppm (b.s., NH$_2$ thiazole) - 1H at 6.69 ppm (S, H thiazole) - 1H at 5.84 ppm (D of D, J$_1$=9 Hz, J$_2$=4 Hz, H$_7$) - 2H at 5.17 ppm (M, H$_6$ and CH$_2$OCO) - 1H at 4.84 ppm (D, J=13 Hz, CH$_2$OCO) - 1H at 4.25 ppm (M, CH—NH$_3^+$)
|
CH$_2$OH -2H at 3.75 ppm (D, J=6 Hz, CH—NH$_3^+$)
|
CH$_2$OH

- 2H at 3.68 ppm (AB, J$_{AB}$=17 Hz, CH$_2$S) - 6H at 1.35 ppm (S, C(CH$_3$)$_2$)

NMR SPECTRUM No. 16: 1H at 10.57 ppm (b.s., OH) - 1H at 9.98 ppm (S, ArNHCO) - 1H at 9.40 ppm (D, J=9 Hz, CONH) - 2H at 8.80 ppm (b.s., CH$_2$NH$_2^+$-CH$_3$) - 1H at 8.08 ppm (D, J=8 Hz, aromatic H ortho NH) - 2H at 7.45 ppm (M, aromatic protons meta NH) - 2H at 7.25 ppm (b.s., NH₂ thiazole) - 1H at 6.68 ppm (S, H thiazole) - 1H at 5.82 ppm (D of D, J₁=9 Hz, J₂=4 Hz, H₇) - 2H at 5.18 ppm (M, H₆ and CH₂OCO) - 1H at 4.83 ppm (D, J=13 Hz, CH₂OCO) - 2H at 4.00 ppm (M, CH₂NH₂+CH₃) - 2H at 3.61 ppm (AB, J_{AB}=17 Hz, CH₂S) - 3H at 2.57 ppm (b.s., CH₂NJ₂⁺—CH₃) - 6H at 1.37 ppm (2S, C(CH₃)₂)

NMR SPECTRUM No. 17: 1H at 10.42 ppm (b.s., OH) - 1H at 9.57 ppm (S, ArNHCO - 1H at 9.43 ppm (D, J=9 Hz, CONH) - 2H at 8.50

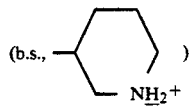

- 1H at 8.05 ppm (D, J=8 Hz, aromatic H ortho NH) - 4H at 7.40 ppm (M, NH₂ thiazole and aromatic protones meta NH) - 1H at 6.69 ppm (S, H thiazole) - 1H at 5.84 ppm (D of D, J₁=9 Hz, J₂=4 Hz, H₇) - 2H at 5.20 ppm (M, H₆ and CH₂OCO ) - 1H at 4.82 ppm (D, J=13 Hz, CH₂OCO) - 2H at 3.66 ppm (AB, J_{AB}=1 Hz, CH₂S) - 5H between 2.5 and 3.5 ppm

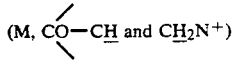

- 4H between 1.45 and 2.05 ppm (CH₂ of the ring meta and para to N+) - 6H at 1.40 ppm (2S, C(CH₃)₂)

NMR SPECTRUM No. 18: 1H at 10.80 ppm (b.s., OH) - 1H at 10.00 ppm (S, ArNHCO) - 1H at 9.44 ppm (D, J=9 Hz, CONH) - 3H at 8.20 ppm (b.s., NH₃⁺) - 1H at 8.05 ppm (D, J=8 Hz, aromatic H ortho NH) - 3H at 7.70 ppm (b.s., NHHU +) - 4H at 7.30 ppm (NH₂ thiazole and aromatic protons meta NH) - 1H at 6.66 ppm (S, H thiazole) - 1H at 5.82 ppm (D of D, J₁=9 Hz, J₂=4 Hz, H₇) - 2H at 5.20 ppm (M, H₆ and CH₂OCO) - 1H at 4.42 ppm

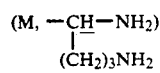

- 2H at 3.61 ppm (AB, J_{AB}=17 Hz, CH₂S) - 2H at 2.83 ppm

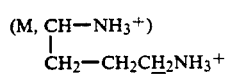

- 2H at 1.80 ppm

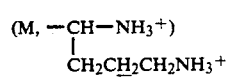

- 2H at 1.60 ppm

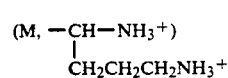

- 6H at 1.39 ppm (2S, C(CH₃)₂)

NMR SPECTRUM No. 19: 1H at 10.72 ppm (b.s., OH) - 1H at 10.00 ppm (S, ArNHCO) - 1H at 9.36 ppm (D, J=9 Hz, CONH) - 3H at 8.40 ppm (b.s., NH₃⁺) - 1H at 8.11 ppm (D, J=8 Hz, aromatic H ortho NH) - 3H at 7.90 ppm (b.s., NH₃⁺) - 4H at 7.30 ppm (M, aromatic protons meta NH and NH₂ thiazole) - 1H at 6.66 ppm (S, H thiazole) - 1H at 5.81 ppm (d of D, J₁=9 Hz, J₂=4 Hz, H₇) -2H at 5.15 ppm (M, H₆ and CH₂OCO) - 1H at 4.82 ppm (D, J=13 Hz, CH₂OCO) - 1H at 4.33 ppm

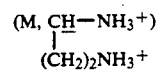

- 2H at 3.64 ppm (AB, J_{AB}=17 Hz, CH₂S) - 2H at 2.90 ppm

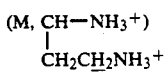

- 2H at 2.15 ppm

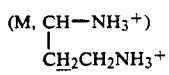

- 6H at 1.39 ppm (2S, C(CH₃)₂)

NMR SPECTRUM No. 20: 1H at 10.80 ppm (S, OH) - 1H at 10.05 ppm (S, ArNHCO) -1H at 9.62 ppm (D, J=9 Hz, CONH - 3H at 8.40 ppm (b.s., NH₃⁺) - 1H at 8.10 ppm (D, J=8 Hz, aromatic H para OH) - 3H at 7.85 ppm (b.s., NH₂⁺) - 2H at 7.45 ppm (M, aromatic protons) - 2H at 7.20 ppm (b.s., NH₂ thiazole) - 1H at 6.66 ppm (s, H thiazole) - 1H at 5.76 ppm (D of D, J₁=9 Hz, J₂=4 Hz, H₇) - 2H at 5.14 ppm (M, H₆ and CH₂ OCO) - 1H at 4.95 ppm (D, J=13 Hz, CH₂OCO) - 1H at 4.35 ppm

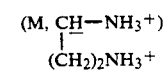

- 3H at 3.81 ppm (S, NOCH₃) - 2H at 3.60 ppm (M, CH₂S) - 2H at 2.88 ppm

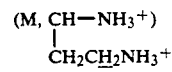

- 2H at 2.06 ppm

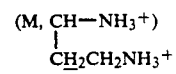

NMR SPECTRUM No. 21: 1H at 10.75 ppm (b.s., OH) - 1H at 10.01 ppm (S, ArNHCO) - 1H at 9.58 ppm (D, J=9 Hz, CONH) - 3H at 8.40 ppm (b.s., NH₃⁺) - 1H at 8.09 ppm (D, J=8 Hz, aromatic H para OH) - 3H at 7.80 ppm (b.s., NH₃⁺) - 2H at 7.46 ppm (M, aromatic protons) - 2H at 7.20 ppm (b.s., NH₂ thiazole) - b'H at 6.71 ppm (S, H thiazole) - 1H at 5.79 ppm (D of D, J₁=90 Hz, J₂=4 Hz, H₇) - 2H at 5.18 ppm (M, H₆ and CH₂OCO) - 1H at 4.92 PPM (d, J=13 Hz, CH₂ OCO) - 1H at 4.30 ppm

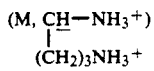

- 3H at 3.82 ppm (S, NOC$\underline{H}_3$) - 2H at 3.60 ppm (AB, $J_{AB}$=17 Hz, C$\underline{H}_2$S) - 2H at 2.78 ppm

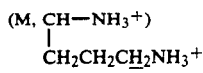

- 2H at 1.80 ppm

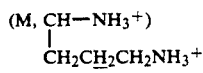

- 2H at 1.62 ppm

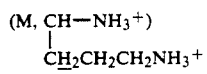

EXAMPLE 16

7-[2-(2-Aminothiazol-4-yl)-2-methoxyiminoacetamido]-3-[[4-(2aminoethylsulfonamido)-3-hydroxybenzoyl]-acetate, syn isomer (SR 44337)

(I) $R_1=R_2=R_3=H$; A=—OH (3); A=—NH-SO$_2$CH$_w$CH$_w$NH$_2$ (4)

A) 3Hydroxy-4-[( 2-tert-butoxycarbonylaminoethyl)-sulfonamido]benzoic acid

1—3-Hydroxy-4-[(2-benzyloxycarbonylaminoethyl)-sulfonamido]benzoic acid 84 g of 4-amino-3-hydroxybenzoic acid are suspended in 1.8 liters of methylene chloride, 228.5 mi of triethylamine are then added under a nitrogen atmosphere and the mixture is cooled to 10° C.

228.5 ml of trimethyichlorosilane are added in 1 hour, with stirring.

The temperature is allowed to return to 20° C. and the mixture is stirred for 2 hours 30 minutes at this temperature.

168 g of 2-benzyloxycarbonylaminoethane sulfochloride are then added with protection from the light and the reaction mixture is stirred at room temperature for 6 hours. It is poured into 2 liters of sulfate buffer of pH 2 and 2 liters of ethyl acetate. The organic phase is separated off, washed with water and dried over ,magnesium sulfate. The solvent is evaporated off to dryness and the residue is taken up in 500 ml of ether. The solid is filtered off, rinsed with isopropyl ether and then dried. Weight: 64.5 g.

A second crop of the same product (54g) is isolated by concentration of the mother dryness and treatment of the residue with isopropyl ether to which a small amount of ether has been added. The 2 crops are combined and dissolved in 470 ml of ethanol. 1.5 liters of water are added slowly and the solution is stirred at room temperature for 30 minutes and then cooled in ice.

The product is filtered off, rinsed with water and dried under vacuum over phosphorus pentoxide. Weight: 102.2 g. Melting point: 194° C.

2—3-Hydroxy-4-(2-aminoethylsulfonamido)benzoic acid trifluoromethylsulfonate.

102 g of the product obtained in A) are added, with stirring, to a mixture of 1 liter of trifluoroacetic acid, 110 mi of trifluoromethanesulfonic acid and 150 mi of thioanisole, cooled to 1° C.

The temperature rises to 20° C. and the mixture is stirred for 1 hour at this temperature.

The product crystallizes and the mixture has to be diluted with 4 liters of methylene chloride. Stirring is continued for 15 minutes, after which the solid is filtered off, rinsed with methylene chloride and then dried under vacuum. Weight: 103.8 g. Melting point: 240° C. (decomposition).

3—3-Hydroxy-4-[(2-tert-butoxycarbonylaminoethyl)sulfonamido]benzoic acid 100 g of the trifluoromethylsulfonate obtained above are dissolved in I liter of water, the pH is adjusted @-o by the addition of a concentrated solution of sodium hydroxide, and 500 ml of dioxane are then added.

A solution of 65 g of ditert-butyl dicarbonate in 300 mi of dioxane is added in 15 minutes, the pH being kept at 7.5 by the addition of sodium hydroxide.

After 30 minutes, the pH remains stable. The reaction mixture is washed with 2.5 liters of ether and the aqueous phase is then poured into layers of sulfate buffer of pH 2.

The pH is adjusted to 2 by the addition of a solution of potassium bisulfate and extraction is then carried out with 2 lifers of ethyl acetate. A second extraction is carried out with I liter of ethyl acetate and the organic extracts are combined. The combined extracts are washed with I liter of a saturated solution of sodium chloride and the organic solution is dried over magnesium sulfate. It is evaporated to dryness and the solid residue is taken up in 1 liter of acetonitrile. The solution is stirred for 15 hours at room temperature and then cooled in ice and the solid is filtered off, washed with isopropyl ether and dried. Weight: 78 g. Melting point: 228–230° C. (decomposition).

B) Tert-butyl 7-[2-(2-tritylaminothiazol-4-yl)-2-methoxyiminoacetamido]-3-[[4-(2-tert-butoxycarbonylaminoethylsulfonamido)-3-hydroxybenzoyl]oxymethyl]-3-cephemcarboxylate, syn isomer.

37.5 g of the protected acid prepared in A) and 15 ml of diisopropylethylamine are dissolved in 200 ml of dimethylformamide. The mixture is cooled to a temperature of between 0 and +5° C. and 60 g of tertbutyl 7-[2-(2-tritylaminothiazol-4-yl)-2-methoxyiminoacetamido]-3-iodomethyl-3-cephem-4-carboxylate, syn isomer, are added.

The reaction mixture is stirred at 0°-5° C. for 5 hours and then poured into 2 liters of iced water. The precipitate is filtered off and rinsed with water. The solid is dissolved in methylene chloride, the solution is dried over magnesium sulfate and the solvent 4-s evaporated off to dryness. The residue is chromatographed on a column of silica H (1 kg). impurities are removed by elution with a 99.1/0.9 vol/vol mixture of methylene chloride and methanol and the expected product is then obtained with a 98/2 vol/vol mixture of the same solvents.

30.7 g are obtained after evaporation of the solvents and washing with isopropyl ether.

C) SR 44337

35 g of the protected product prepared above in B) are added, with stirring, to a mixture of 330 ml of trifluoroacetic acid and 33 mi of anisole, cooled in an ice bath.

The temperature is allowed to rise to 20° C. and the mixture is stirred for 1 hour at this temperature.

It is poured into 1.5 liters of isopropyl ether cooled to 0° C.

The precipitate is filtered off, washed with ether and then dried under vacuum over phosphorus pentoxide.

26.8 g of the expected product are obtained.

This is dissolved in 100 ml of methanol and the solution is poured into 1.25 l of ether. The precipitate is filtered off, rinsed with ether and dried under vacuum and 22 g of the title product are finally obtained.

NMR SPECTRUM: 1 H at 10.7 ppm (S.b., N$\underline{H}$—SO$_2$) - 1 H at 9.6 ppm (D, J=8 Hz, —N$\underline{H}$CO—) - 1 H at 9.5 ppm (S.b., —O$\underline{H}$) - 9 H between 7 and 8.2 ppm (M, 3 H aromatic and 2NH$_2$) - 1 H at 6.7 ppm (S, $\underline{H}$ thiazole) - 1 H at 5.75 ppm (D of D, J$_1$=8 Hz, J$_2$=4 Hz, H$_7$) - 1 H at 5.15 ppm (D, J=4 Hz, H$_6$) - 2 H at 4.9 and 5.2 ppm (AB, J$_{AB}$=14 Hz, C$\underline{H}_2$OCO) - 3 H at 3.8 ppm (S, NOC$\underline{H}_3$) - 6 H between 3.1 and 3.75 ppm (M, C$\underline{H}_2$NH$_2$, C$\underline{H}_2$SO$_2$, C$\underline{H}_2$S).

EXAMPLE 17

7-[2-(2-Aminothiazol-4-yl)-2-methoxyiminoacetamido]-3-[[4-(2-aminoethylsulfonamido)-3-hydroxybenzoyl]oxymethyl]-3-cephem-4-carboxylic acid bishydrochloride, syn isomer.

10.53 g of the protected product obtained in Example 1 B are dissolved in 60 ml of 98% formic acid and the solution is stirred for 2 hours at 200° C. 50 ml of a 10 N aqueous solution of hydrochloric acid are added and the mixture is stirred for a further 2 hours at 20° C.

The reaction mixture is poured into 500 ml of ethyl ether. The bis-hydrochloride is filtered off, washed with ether and dried under vacuum.

7 g of the expected product are obtained. Melting point: 145°C. (decomposition).

NMR SPECTRUM: 1 H at 9.8 ppm (D, J=8 Hz, N$\underline{H}$CO) - 6 H at 8.2 ppm (M, 2N$\underline{H}_3^+$) - 3 H between 7.2 and 7.6 ppm (M, H aromatic) - 1 H at 6.9 ppm (S, H thiazole) - 1 H at 5.8 ppm (D of D, J$_1$=8 Hz, J$_2$=4 Hz, H$_7$) - 1 H at 5.2 ppm (D, J=4 Hz, H$_6$) - 2 H between 4.9 and 5.2 ppm (AB, J$_{AB}$=14 Hz, CH$_2$—S) - 4 H between 3.2 and 3.5 ppm (M, —C$\underline{H}_2$C$\underline{H}_2$NH$_2$)

EXAMPLE 18

Inner salt of 7-[2-(2-aminothiazol-4-yl)-2-methoxyiminoacetamido]-3-[[4-(2-aminoethylsulfonamido)-3-hydroxybenzoyloxymethyl]-3-cephem-4-carboxylic acid, syn isomer.

1 g of the bis-trifluoroacetate obtained in Example 16 C is dissolved in 10 ml of anhydrous dimethylformamide, the solution is cooled to 5° C. and a solution of 0.24 g of diethanolamine in 2 ml of methanol is then added. The mixture is stirred for 15 minutes at 5° C. and then poured in to 100 ml of ether cooled to 5° C. The solid is filtered off and dried under vacuum in the presence of phosphorus pentoxide. 0.800 g of inner salt is obtained.

NMR SPECTRUM: 1 H at 9.5 ppm (D, J=8 Hz, NHCO) - 1 H between 7.5 and 11 ppm (S.b., O$\underline{H}$) - 3 H between 7 and 7.5 ppm (M, H aromatic) - 1 H at 6.7 ppm (S, H thiazole) - 1 H at 5.6 ppm (D of D, J$_1$=8 Hz, J$_2$=4 Hz, H$_7$) -1 H at 5.05 ppm (D, J=4 Hz, H$_6$) - 2 H at 4.85 and 5.15 ppm (AB, J$_{AB}$=14 Hz, C$\underline{H}_2$OCO) - 3 H at 3.12 ppm (M, NOC$\underline{H}_3$) - 2 H at 3.6 ppm (S, C$\underline{H}_2$S) - 2 H at 3.12 ppm (M, C$\underline{H}_2$SO$_2$NH) - 2 H at 2.95 ppm (M, C$\underline{H}_2$NH$_2$).

EXAMPLE 19

7-[2-(2-Aminothiazol-4-yl)-2(2-carboxyprop-2-yloxyimino)acetamido]-3- cephem-4-carboxylic acid bis-trifluoroacetate, syn isomer (SR 44338).

(I) R$_1$=R$_2$=CH$_3$; R$_3$=COOH: A=OH (3); A=—NHSO$_2$CH$_2$CH$_2$NH$_2$ (4)

This product is prepared in the same way as the product of Example 16, the tert-butyl 7-[2-(2-tritylaminothiazol-4-yl)-2-methoxyiminoacetamido]-3-iodomethyl-3-cephem-4-yl )-2-methoxyiminoacetamide]-3-iodomethyl-3-cephem-4-carboxylate, syn isomer, being replaced in step B with an equivalent amount of tert-butyl 7-prop-2-yloxyimino)acetamido]-3-iodomethyl-3-cephem-4-carboxylate, syn isomer.

The product SR 44338 is obtained after deprotection as indicated in Examples 16 C.

NMR SPECTRUM: 1 H at 9.4 ppm (D, J=8 Hz, CON$\underline{H}$) - 11 H between 7 and 11 ppm (M, 3 $\underline{H}$ aromatic, N$\underline{H}_2$, O$\underline{H}$ 2NH$_3$) -1 H at 6.7 ppm (S, $\underline{H}$ thiazole) - 1 H at 5.8 ppm (d of D, J$_1$=8 Hz, J$_2$=4 Hz, H$_7$) - 1 H at 5.2 ppm (D, J=4 Hz, H$_6$) - 2 H at 4.9 and 5.25 ppm (AB, J$_{AB}$=14 Hz, CH$_2$ OCO)-6H between 3.1 and 3.75 ppm (M, C$\underline{H}_2$NH$_2$, $\overline{C}$H$_2$SO$_2$, C$\underline{H}$S) - 6 H at 1.4 and 1.42 ppm $$(2S, O-C\!\!\begin{array}{c}\diagup C\underline{H}_3 \\ \diagdown CH_3\underline{\phantom{x}}\end{array}\!\!).$$

The products according to the invention were studied for their pharmacological properties.

The bacteriostatic action was determined in vitro by the dilution method. The study was carried out on both Gram-positive strains and Gram-negative strains.

The results for various products according to the invention, expressed as minimum inhibitory concentrations (MIC - μg/ml), are collated in Table 3.

These results show that the products according to the invention have a broad spectrum of activity and possess a very good intrinsic activity.

Furthermore, the pharmacokinetic behavior of the products according to the invention was studied in baboons after, administration at a dose of 20 mg/kg by intramuscular injection or intravenous injection.

Blood samples taken at various times after administration are used to determine the plasma concentration of the product studied by microbiological assay.

It is thus possible to construct the curve showing the plasma concentration as a function of time, and to determine different pharmacokinetic parameters of the compound studied:

the elimination half-life (t½ β) is calculated by the formula $$\frac{\ln 2}{\beta},$$

in which β represents the elimination gradient or slope;

TABLE 3

| STRAIN | PRODUCT SR N° | | | | | | | | |
|---|---|---|---|---|---|---|---|---|---|
| | 43753 | 43852 | 43904 | 43853 | 44128 | 44219 | 44130 | 44218 | 44337 |
| Staph. aureus Smith | 2 | 0.25 | 4 | 0.25 | 8 | 0.5 | 8 | 0.5 | 0.25 |
| Escherichia coli C1/Col E1::Tn3 | 0.12 | 0.06 | 0.25 | 0.06 | 0.12 | 0.12 | 0.25 | 0.25 | 0.06 |
| Escherichia coli SOL RL 90 | 2 | 0.25 | 2 | 0.25 | 2 | 0.12 | 2 | 0.5 | 0.5 |
| Klebsiella pneumoniae R30 | 1 | 4 | 1 | 4 | 1 | 4 | 1 | 8 | 4 |
| Proteus vulgaris GN 76/C-1 | 0.12 | 16 | 0.25 | 16 | 0.12 | 16 | 0.12 | 16 | 1 |
| Providencia 155 | 1 | 2 | 1 | 1 | 1 | 1 | 1 | 2 | 1 |
| Pseudomonas aeruginosa NCTC 8203 | 2 | 2 | 1 | 2 | 2 | 1 | 2 | 4 | 2 | the area under the curve (AUC) is determined by the trapezium method.

Furthermore, the protein binding is obtained by comparing two standard scales, one being prepared in baboon plasma and the other in phosphate buffer (pH 7, 0.03 M).

The plasma concentrations obtained with various products of the invention are collated in Tables 4 and 5. They are expressed in μg/ml.

For the purpose of comparison, these tables include the results obtained with 3 products of the prior art, corresponding respectively to the formulae:

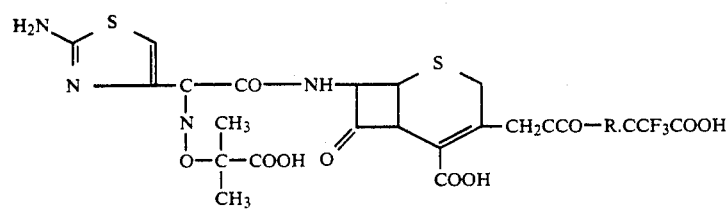

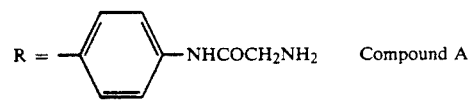  Compound A

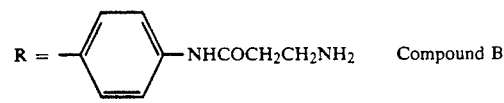  Compound B

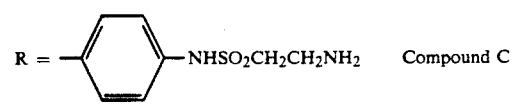  Compound C

TABLE 4-continued

| TIME (minutes) | PRODUCT | | | | | |
|---|---|---|---|---|---|---|
| | SR 43753 | SR 43904 | SR 44128 | SR 44130 | A | B |
| 360 | 80.9 | 34.3 | 104.7 | 90.4 | 17.3 | 4.8 |

ND = not determined

TABLE 5

| | μg/ml | |
|---|---|---|
| TIME (hours) | SR 44337 (Example 16) | Compound C |
| 0.08 | 265.5 | 232.8 |
| 0.16 | 250.9 | 212.6 |
| 0.25 | 237.5 | 189.7 |
| 0.33 | 206.1 | 170.4 |
| 0.5 | 194.3 | 124.2 |
| 0.75 | 190.0 | 120.7 |
| 1 | 182.5 | 119.8 |
| 1.5 | 163.8 | 112.4 |
| 2 | 152.7 | 98.4 |
| 3 | 151.7 | 72.9 |
| 4 | 146.7 | 68.7 |
| 5 | 141.1 | 62.1 |
| 6 | 120.1 | 54.4 |
| 24 | 39.0 | 7.7 |
| 48 | 14.4 | 0.6 |

TABLE 4

| TIME (minutes) | PRODUCT | | | | | |
|---|---|---|---|---|---|---|
| | SR 43753 | SR 43904 | SR 44128 | SR 44130 | A | B |
| 10 | 36.8 | 12.6 | 62.9 | 39.1 | 20.8 | 8.5 |
| 20 | 69.1 | ND | 115.3 | 60.9 | 36.8 | 16.4 |
| 30 | 95.2 | 52.4 | 134.8 | 81.9 | 44.4 | 16.9 |
| 45 | 128.6 | 73.0 | 176.6 | 104.7 | 59.3 | 17.6 |
| 60 | 139.2 | 76.1 | 187.9 | 121.6 | 60.0 | 20.7 |
| 90 | 146.0 | 94.1 | 187.8 | 143.4 | 55.5 | 24.1 |
| 120 | 151.1 | 76.1 | 194.6 | 141.6 | 53.3 | 20.7 |
| 180 | 126.1 | 59.7 | 168.8 | 137.8 | 40.0 | 17.6 |
| 240 | 120.9 | 57.3 | 141.9 | 134.8 | 36.2 | 12.5 |
| 300 | 112.6 | 53.4 | 123.0 | 109.1 | 27.2 | 8.3 |
| 330 | 97.6 | 39.9 | ND | 93.8 | 23.7 | 6.8 |

The pharmacokinetic parameters of the products according to the invention and the comparison products, determined according to the same experience, have been collated in Tables 6 and 7 below.

TABLE 6

| PARAMETERS | PRODUCTS | | | | | |
|---|---|---|---|---|---|---|
| | SR 43753 | SR 43904 | SR 44128 | SR 44130 | A | B |
| Max plasma concentration (μg/ml) | 151.1 | 94.1 | 194.6 | 143.4 | 69.5 | 24.1 |
| T max (min) | 120 | 90 | 120 | 90 | 45 | 90 |
| Plasma concentration at 6 h (μg/ml) | 80.9 | 34.3 | 104.5 | 90.4 | 17.3 | 4.8 |
| $t_{\frac{1}{2}} \beta$ (min) | NC | 265 | NC | NC | 195 | 99 |
| AUC 0–6 hr ($\mu g \cdot ml^{-1} \cdot min$) | 42178 | 20859 | 53890 | 42403 | 17033 | 5276 |
| Excretion in the urine (% dose, 6 h) | 18 | 17 | 72 | 37 | 23 | 18 |
| Protein binding (%) | 84 | 71 | 84 | 92 | 45 | 48 |

NC: not calculable

TABLE 7

| Parameter | Product | |
|---|---|---|
| | SR 44337 (Example 16) | Compound C |
| Maximum plasma (μg/ml) | 265.5 | 232.8 |
| Plasma concentration (μg/ml) | | |
| at 24 h | 39.0 | 7.7 |
| at 48 h | 14.4 | 0.6 |
| $t_{\frac{1}{2}} \beta$ (h) | 13.9 | 6.3 |
| AUC 0–∞ (μg/ml × h) | 3316 | 1210 |
| Excretion in urine (% dose) at 6 h | 14 | 18 |

The results given in Tables 4 through 7 show that the plasma concentrations of products of the invention are extremely high and long-lasting.

If a comparison is made with the reference products A and B, the 6-hour plasma concentrations obtained for their hydroxylated homologs are respectively 4.6 and 7 times higher. Likewise, if the area under the curve is considered, the increase is respectively 2.5 and 4 times, compared with the reference products.

When compared with reference product C, the plasma concentrations at 24 and 48 hours obtained for the compound of Example 16 are respectively 5 and 24 times higher. Likewise, as regards the area under the curve, the increase is 2.7-fold relative to the reference product.

The compounds according to the invention therefore have very advantageous pharmacokinetic parameters which make it possible substantially to reduce the amount of active principle used and the number of daily administrations which are necessary for a given therapeutic effect.

Finally, the toxicity of the products according to the invention is sufficiently low for them to be used in therapy.

The products of the invention can therefore be employed as antibiotics in human or veterinary medicine. They have a broad spectrum and can be used for all bacterial infections caused by sensitive germs.

The products can be administered by a general route (parenteral, oral, rectal) or topically.

The pharmaceutical compositions are prepared from the compounds (I) in a soluble form obtained by salification of at least one of the acid groups or amine groups present therein.

The pharmaceutical compositions containing the antibiotic according to the invention as the active ingredient, in combination with a pharmaceutically acceptable vehicle, can be solid or liquid and can take the form of, for example, injectable preparations, tablets, gelatine capsules, granules, ointments, creams, gels or suppositories. They contain, for example, from 50 to 1000 mg. of active principle. The dosage can vary within wide limits, in particular depending on the type and severity of the infection to be treated and depending on the method of administration.

Most frequently, the adult dosage for administration by injection is between 0.250 g and 4 g per day.

As examples of pharmaceutical preparations, it is possible to prepare an injectable solution containing the following in each ampoule:

|  | SR 43753 | 1 g |
|---|---|---|
|  | Water for injectable preparations | 5 ml |
|  | Sodium carbonate q.s. for pH = | 6.3 |
| or | | |
|  | SR 44337 | 1 g |
|  | Water for injectable preparations | 5 ml |
|  | Sodium carbonate q.s. for pH = | 6.3 |

What is claimed is:

1. A compound corresponding to the formula

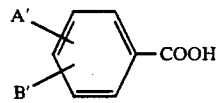

in which the groups A' and B' are different and occupy the meta and para positions on the benzene ring, one of them representing a group OH and the other representing a group X—NH—Alk—SO$_2$—NH—, in which X represents hydrogen or a protecting group for the amine group and Alk represents a C$_2$–C$_4$ lower alkylene group.

* * * * *